US005742422A

United States Patent [19]

Drake

[11] Patent Number: 5,742,422

[45] Date of Patent: Apr. 21, 1998

[54] ADJUSTABLE FOURIER MASK

[75] Inventor: Steven R. Drake, Concord, Mass.

[73] Assignee: Inspex, Inc., Billerica, Mass.

[21] Appl. No.: 530,051

[22] Filed: Sep. 19, 1995

[51] Int. Cl.$^6$ .............................. G01N 21/00; G02B 27/46

[52] U.S. Cl. .......................... 359/227; 359/559; 359/562; 356/237

[58] Field of Search .............................. 356/71, 329, 237, 356/239; 359/227, 230, 231, 232, 234, 559, 562

[56] References Cited

U.S. PATENT DOCUMENTS

| | | | |
|---|---|---|---|
| 2,844,069 | 7/1958 | Azarraga | 359/234 |
| 3,409,872 | 11/1968 | Hogg et al. | 356/71 |
| 3,537,777 | 11/1970 | Flynn | 359/232 |
| 3,614,232 | 10/1971 | Mathisen | 356/71 |
| 3,639,039 | 2/1972 | Rhodes, Jr. | 359/559 |
| 3,658,420 | 4/1972 | Axelrod | 356/71 |
| 3,860,328 | 1/1975 | Firth | 359/232 |
| 4,330,775 | 5/1982 | Iwamoto et al. | 356/71 |
| 4,360,269 | 11/1982 | Iwamoto et al. | 356/239 |
| 4,806,744 | 2/1989 | Liu et al. | 250/550 |
| 4,895,446 | 1/1990 | Maldari et al. | 356/336 |
| 5,172,000 | 12/1992 | Scheff et al. | 356/237 |
| 5,317,380 | 5/1994 | Allemand | 356/338 |
| 5,475,459 | 12/1995 | Matsubara et al. | 359/234 |

FOREIGN PATENT DOCUMENTS

| | | | |
|---|---|---|---|
| A 0076088 | 6/1977 | Japan | 359/559 |
| A 5-93696 | 4/1993 | Japan | 359/559 |

*Primary Examiner*—Paul M. Dzierzynski
*Assistant Examiner*—John Juba, Jr.
*Attorney, Agent, or Firm*—Kriegsman & Kriegsman

[57] ABSTRACT

A Fourier mask includes a base plate, an aperture plate having a pair of cross hairs fixedly mounded on the base plate and a pair of four bar linkages, each four bar linkage being made up of a pair of parallel cross bars and a pair of parallel mask bars pivotally interconnected end-to-end in a closed loop configuration. Each cross bar in each four bar linkage is pivotally mounted on the base plate, the four bar linkages being arranged on the base plate such that the mask bars in one four bar linkage are at right angles to the mask bar in the other four bar linkage and each pair of parallel mask bars is symmetrically disposed about one of the cross hairs. By pivotally moving either or both sets of cross bars on the base plate, the spacing between the parallel mask bars in either a both sets of mask bars can be changed as desired.

12 Claims, 4 Drawing Sheets

ADJUSTABLE FOURIER MASK

BACKGROUND OF THE INVENTION

The present invention relates generally to Fourier masks and, more particularly, to a Fourier mask which is adjustable.

There are a variety of existing ways for detecting and measuring the number and sizes of particles on the surface of a patterned semiconductor wafer for the purpose of rejecting those wafers which have on their surface one or more particles above certain sizes or an excessive number of particles. One of the more simple methods involves having a human operator inspect the wafer using a light field/dark field microscope. Using the eye, the operator actually counts the number of particles and also identifies the size of the particles, such as those between 1 and 20 microns, and then rejects those wafers which have particles of or above a certain size or which have an excessive number of particles. This method, however, is highly inaccurate and very expensive both in terms of wages for the human operator and in terms of the number of rejects both after the inspection and after production of the chips (when an erroneously passed wafer is found to have an electrical defect, e.g., short circuits, because of the presence of contaminant particles).

Accordingly, a number of systems have been developed for detecting the presence of particles on the surface of a patterned semiconductor wafer; most of such systems involving the principle of light scattering. Several of these systems have included the use of a mask in a plane on the output side of a lens used to image light diffracted from the surface being examined, to block off diffracted light from the pattern on the wafer but not diffracted light from a particle which might be present on the surface of the wafer. The mask is commonly referred to as a "Fourier mask". The Fourier transform caused by the pattern lines on the wafer and which the mask is used to block is usually made up of two groups of light bars, each group comprising a plurality of parallel equally spaced light bars, the two groups being perpendicular to each other. The spacing between the light bars in each group will vary, depending on the particular pattern of lines on the surface of the wafer being examined.

In U.S. Pat. No. 5,317,380, issued May 31, 1994, and assigned to Inspex, Inc. there is disclosed a method and apparatus for detecting particles on a surface of an object, such as a virgin or patterned semiconductor wafer, ceramic tile, or the like. In one embodiment, an apparatus is provided in which a scanning beam of laser light is brought to focus as an arcuate scan line on a surface of the object at a grazing angle of incidence using an off-axis hypertelecentric mirror. A pair of light detectors are positioned at a meridional angle of about 30 degrees and at an azimuthal angle of about 4 degrees to measure forward scattered light to the surface. The object is then moved translationally so that the beam can scan another line of the surface. A light trap is provided to trap light that is reflected by the surface and a series of masks are provided to mask light which is scattered by the hypertelecentric mirror and in the case of pattered objects, light which is diffracted by the pattern imprinted on the object.

In U.S. Pat. No. 4,806,744 issued Feb. 21, 1989 and assigned to Insystems, Inc., there is disclosed an inspection system which employs a Fourier transform lens and an inverse Fourier transform lens positioned along an optic axis to produce from an illuminated area of a patterned specimen wafer a spatial frequency spectrum whose frequency components can be selectively filtered to produce an image pattern of defects in the illuminated area of the wafer. Depending on the optical components configuration of the inspection system, the filtering can be accomplished by a spatial filter of either the transmissive or reflective type. The lenses collect light diffracted by a wafer die aligned with the optic axis and light diffracted by other wafer dies proximately located to such die. The inspection system is useful in inspecting only dies having many redundant circuit patterns. The filtered image strikes the surface of a two-dimensional photodetector array which detects the presence of light corresponding to defects in only the illuminated on-axis wafer die. Inspection of all possible defects in the portions of the wafer surface having many redundant circuit patterns is accomplished by mounting the wafer onto a two-dimensional translation stage and moving the stage so that the illuminated area continuously scans across the wafer surface from die to die until the desired portions of the wafer surface have been illuminated. The use of a time delay integration technique permits continuous stage movement and inspection of the wafer surface in a raster scan fashion.

In U.S. Pat. No. 4,895,446 to M. C. Maldari et al., there is disclosed a method and apparatus for detecting the presence of particles on the surface of an object such as the front side of a patterned semiconductor wafer. A vertically expanded, horizontally scanning, beam of light is directed onto an area on the surface of the object at grazing angle of incidence. A video camera positioned above the surface detects light scattered from any particles which may be present on the surface, but not specularly reflected light. The surface is angularly repositioned (rotated) relative to the incident light beam so that the diffracted light from the surface and the pattern of lines on the surface is at a minimum. The object is then moved translationally to expose another area to the incident light beam so that the entire surface of the object or selected portions thereof can be examined, one area at a time. The patent also discloses the use of a mask containing a pattern corresponding to the Fourier transform of the patterned surface to mask off light scattered from the pattern on the surface but not any particles that may be present on the surface.

In U.S. Pat. No. 3,614,232 to E. S. Mathisen, defects in microcircuit patterns are sensed by illuminating the pattern with monochromatic collimated light. The illuminated pattern is imaged through a lens to produce substantially a two-dimensional optical Fourier transform of the pattern at a plane on the output side of the lens. An optical filter (transparency) which includes substantially the negative of the Fourier transform of a defect-free specimen of the microcircuit is placed at the aforesaid plane to block the optical frequency components corresponding to the defect-free specimen. Light passing through the filter is processed to provide various indications of the pattern defects.

SUMMARY OF THE INVENTION

It is an object of the present invention to provide a new and improved Fourier mask for use in an apparatus for detecting the presence of contaminant particles on the surface of a patterned semiconductor wafer having repetitive patterns using the principle of scattered light.

It is another object of the present invention to provide a Fourier mask which is adjustable.

It is a further object of this invention to provide a Fourier mask which is not limited to use with one particular wafer pattern configuration.

According to one feature of the invention, a Fourier mask is provided which includes a base plate, a first four bar linkage, said first four bar linkage comprising a pair of parallel cross bars and a pair of parallel mask bars, said cross bars and said mask bars being pivotally interconnected end-to-end in a closed loop configuration, a first pivot assembly for pivotally mounting one of said cross bars in said first four bar linkage on said base plate, and a second pivot assembly for pivotally mounting the other one of said cross bars in said first four bar linkage on said base plate, whereby the spacing between said pair of parallel mask bars in said first four bar linkage can be changed by pivotally moving said cross bars in said first four bar linkage on said base plate.

According to another feature of the invention, a Fourier mask is provided which includes a base plate, a first four bar linkage, said first four bar linkage comprising a pair of parallel cross bars and a pair of parallel mask bars, said cross bars and said mask bars being pivotally interconnected end-to-end in a closed loop configuration, a first pivot assembly for pivotally mounting one of said cross bars in said first four bar linkage on said base plate, a second pivot assembly for pivotally mounting the other one of said cross bars in said first four bar linkage on said base plate, whereby, the spacing between said pair of parallel mask bars in said first four bar linkage can be changed by pivotally moving said cross bars in said first four bar linkage on said base plate, a second four bar linkage, said second four bar linkage comprising a pair of parallel cross bars and a pair of parallel mask bars, said cross bars and said mask bars being pivotally interconnected end-to-end in a closed loop configuration, a third pivot assembly for pivotally mounting one of said cross bars in said second four bar linkage on said base plate, and a fourth pivot assembly for pivotally mounting the other one of said cross bar in said second four bar linkage on said base plate, whereby, the spacing between said pair of parallel mask bars in said second four bar linkage can be changed by pivotally moving said cross bars in said second four bar linkage on said base plate, the said mask bars in said first four bar linkage being disposed at right angles to said mask bars in second four bar linkage.

According to still another feature of the invention, a Fourier mask is provided which includes a base plate, an aperture plate mounted on the base plate, the aperture plate having an aperture and a pair of cross bars, a first four bar linkage, said first four bar linkage comprising a pair of parallel cross bars and a pair of parallel mask bars, said cross bars and said mask bars being pivotally interconnected end-to-end in a closed loop configuration, a first pivot assembly for pivotally mounting one of said cross bars in said first four bar linkage on said base plate, a second pivot assembly for pivotally mounting the other one of said cross bars in said first four bar linkage on said base plate, whereby, the spacing between said pair of parallel mask bars in said first four bar linkage can be changed by pivotally moving said cross bars in said first four bar linkage on said base plate, a second four bar linkage, said second four bar linkage comprising a pair of parallel cross bars and a pair of parallel mask bars, said cross bars and said mask bars being pivotally interconnected end-to-end in a closed loop configuration, a third pivot assembly for pivotally mounting one of said cross bars in said second four bar linkage on said base plate, and a fourth pivot assembly for pivotally mounting the other one of said cross bar in said second four bar linkage on said base plate, whereby, the spacing between said pair of parallel mask bars in said second four bar linkage can be changed by pivotally moving said cross bars in said second four bar linkage on said base plate, the said mask bars in said first four bar linkage being disposed at right angles to said mask bars in second four bar linkage.

BRIEF DESCRIPTION OF THE DRAWINGS

In the drawings wherein like reference numerals represent like parts.

DETAILED DESCRIPTION OF PREFERRED EMBODIMENTS

Figure 1:
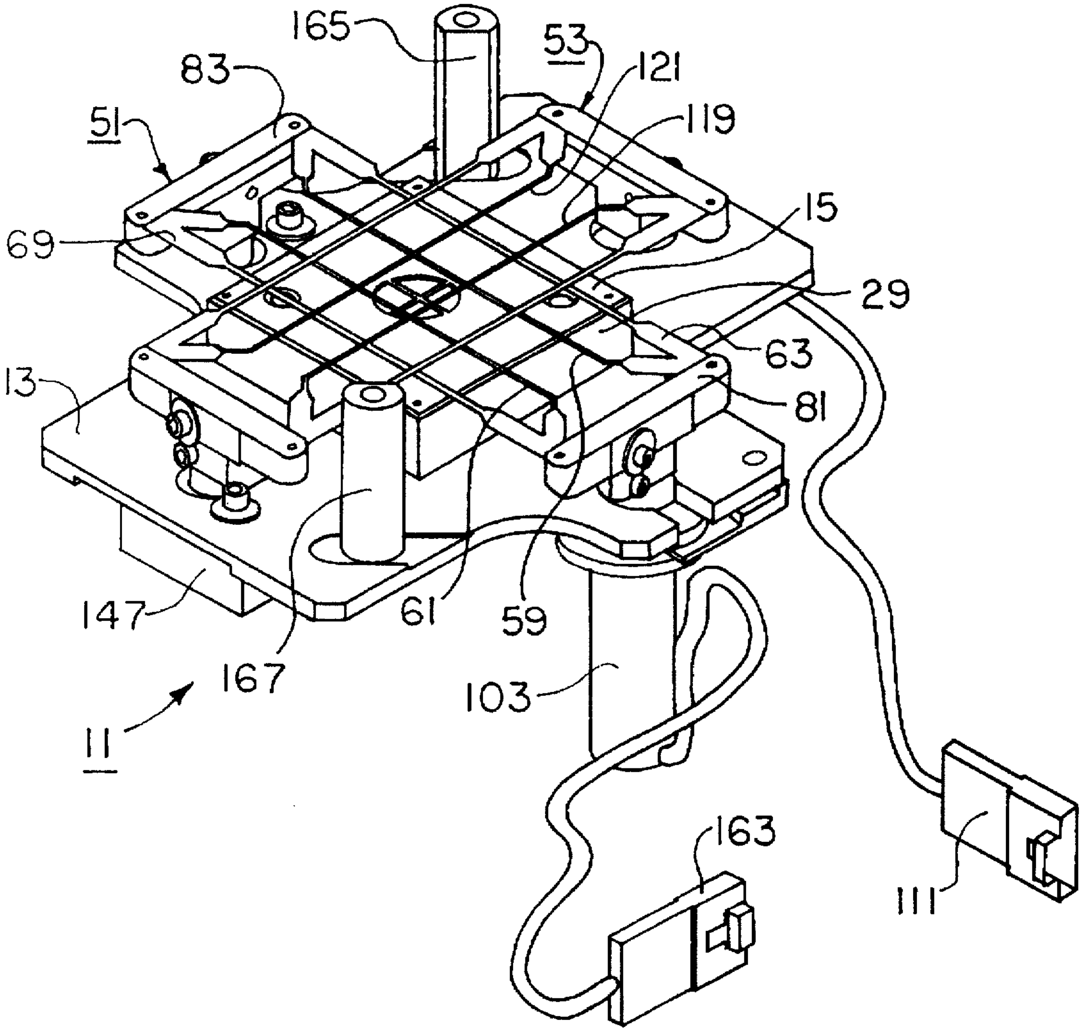
FIG. 1 is a perspective view taken from the top of a Fourier mask constructed according to the teaching of the present invention.
Figure 2:
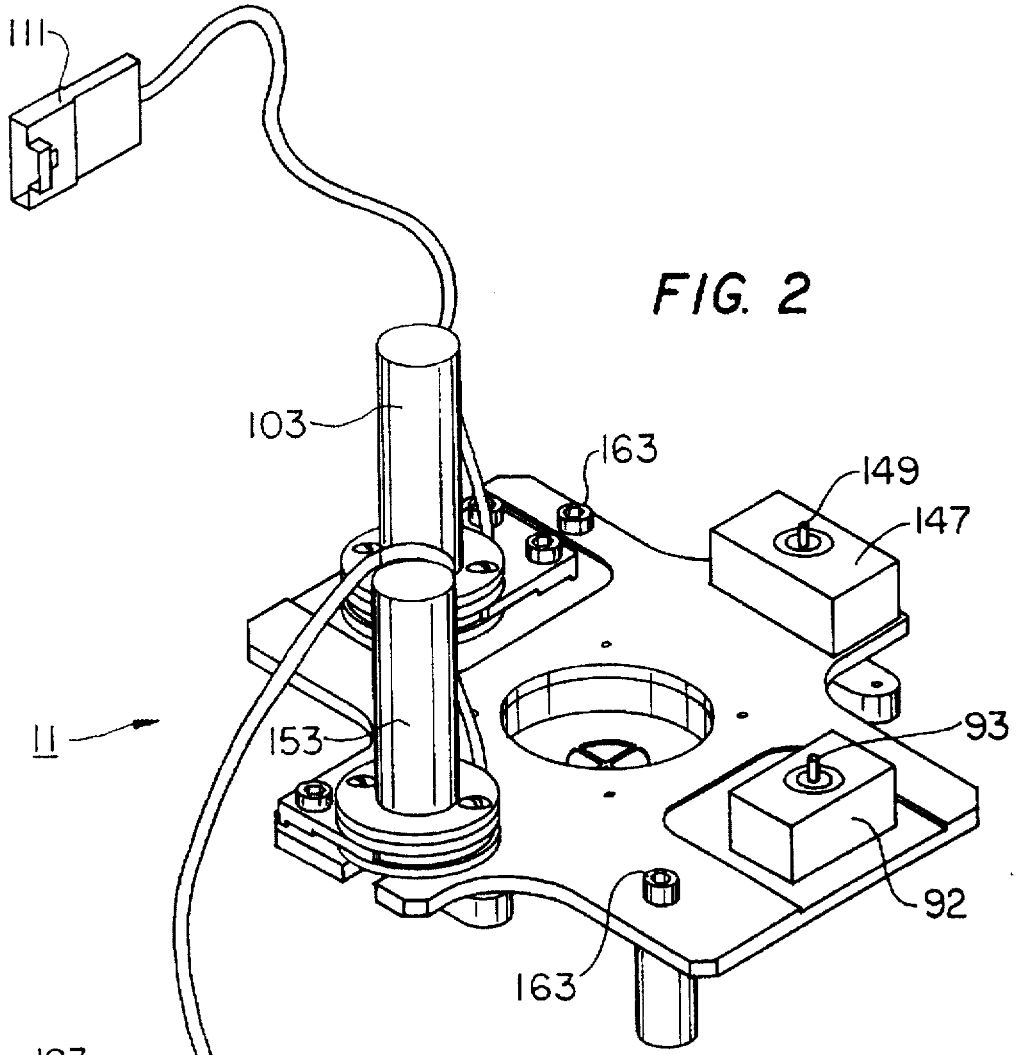
FIG. 2 is a perspective view taken from the bottom of the Fourier mask shown in FIG. 1.

The present invention is directed to a Fourier mask which includes spatially adjustable mask bars.

Referring now to FIGS. 1–5, there is shown an Fourier mask constructed according to the teachings of this invention and identified by reference numeral 11.

Fourier mask 11 includes a base plate 13. An aperture plate 15 is mounted on base plate 13 and secured in place by a pair of screws 17 and 19 which extend through holes 21 and 23, respectively in aperture plate 15, through holes 25 and 27, respectively, in an aperture spacer block 29 disposed between aperture plate 15 and base plate 13 and into threaded holes 31 and 33, respectively, in base plate 13.

Aperture plate 15 is held in place on aperture spacer block 29 by pins 35 which are press fit into holes 37 on aperture plate 15 and holes 39 on aperture spacer block 29. Aperture plate 15 includes an aperture 41 having a set of fixed cross hairs 45, the set including a horizontal cross hair 47 and a vertical cross hair 49.

Fourier mask 11 further includes a first four bar linkage 51 and a second four bar linkage 53.

First four bar linkage 51 includes a pair of parallel cross bars 55 and 57 and a pair of parallel mask bars 59 and 61. Ears 63 and 65 are integrally formed at the ends of mask bar 59 and ears 67 and 69 are integrally formed at the ends of mask bar 61. Ears 63 and 65 are connected by an integrally formed reinforcing bar 71 which is parallel to mask bar 59 and ears 67 and 69 are connected by an integrally formed reinforcing bar 73 which is parallel to mask bar 61. Cross bars 55 and 57 and mask bars 59 and 61 are pivotally interconnected end-to-end in a closed loop configuration by pivot pins 75 which extend through holes 77 formed in 63, 65, 67 and 69 and through holes 79 formed in cross bars 55 and 57. As can be appreciated, mask bars 59 and 61 are always parallel to each other and cross bars 55 and 57 are always parallel to each other. A pair of retainer clips 81 and 83 are provided, one clip 81 for maintaining ears 63 and 67 in place on cross bar 55 and the other clip 83 for maintaining ears 65 and 69 in place on cross bar 57. Clips 81 and 83 clip onto cross bars 55 and 57, respectively, and are secured thereon by screws 85, with pivot pins 75 extending partially up into holes 87 formed in clips 81 and 83.

Adjustable Fourier mask also includes a first pivot assembly 89 for pivotally mounting cross bar 55 on base plate 13 and a second pivot assembly 91 for pivotally mounting cross bar 57 on base plate 13.

First pivot assembly 89 includes a bearing holder 92 and a pivot pin 93. Bearing holder 92 is mounted on base plate 13 by screws 95 which extend down through holes 97 in base plate 13 into threaded holes 99 in bearing holder 92. Pivot pin 93 is pivotally mounted inside bearing holder 92 and extends up through an opening 101 in base plate 13 and into a hole (not shown) extending up from the bottom of cross bar 55.

Second pivot assembly 91 includes an electric motor 103 which is mounted on base plate 13 from the bottom by a motor clamp 105 and screws 107. Motor 103 includes a drive shaft 109 which extends up through an opening 110 formed in base plate 13 and is press fit into a hole (not shown) formed in cross bar 57. Thus, when drive shaft 109 of motor 103 rotates, i.e. turns about its longitudinal axis it will carry with it cross bar 57. Electric motor 103 also includes a connector 111 for connecting motor 103 to a power source. Connector 111 is connected to motor 103 by a pair of wires 113.

Pivot assemblies 89 and 91 are positioned on base plate 13 such that mask bars 59 and 61 are parallel to and symmetrically disposed on either side of horizontal cross hair 47.

Figure 4:
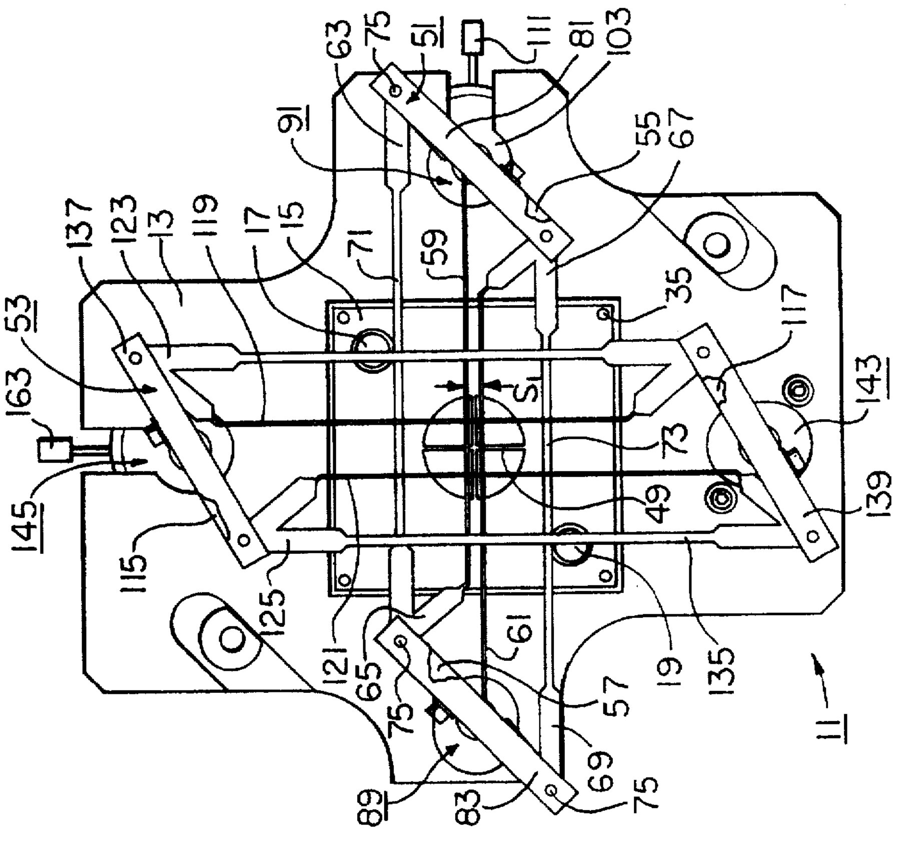
FIG. 4 is a plan view of the Fourier mask shown in FIG. 1.

Also, as can be appreciated, spacing between mask bars 59 and 61 can be easily changed by rotating (i.e. pivotally moving) cross bar 57. In FIG. 4, mask bars 59 and 61 are shown at one spacing $S_1$ and in FIG. 5, mask bars 59 and 61 are shown at another spacing $S_2$. As can also be appreciated, cross hair 47 together with mask bars 59 and 61 provide three parallel mask elements which together can block off three parallel light bars. Also, the space between mask bar 59 and cross hair 47 will also be the same as the spacing between cross hair 47 and mask bar 59, even though the spacing between mask bars 59 and 61 is changed (i.e. either increased or decreased).

Second four bar linkage 53 is identical to first four bar linkage 51 and thus includes a pair of parallel cross bars 115 and 117 and a pair of parallel mask bars 119 and 121 terminating at their ends in ears 123, 125, 127 and 129 and pivotally interconnected end-to-end by pivot pins 131 in a closed loop configuration, reinforcing bars 133, 135 integrally formed on ears 123, 125 and 127 and 129 and retainer clips 137 and 139 attached to cross bars 115 and 117 by screws 141.

Fourier mask 11 further includes a third pivot assembly 143, identical to first pivot assembly 89, for pivotally mounting cross bar 115 on base plate 13 and a fourth pivot assembly 145, identical to second pivot assembly 91 for pivotally mounting cross bars 117 on base plate 13. Third pivot assembly 143 includes a bearing holder 147, a pivot pin 149 and mounting screws 151 corresponding to bearing holder 91, pin 93 and screws 95, respectively. Fourth pivot assembly 145 includes an electric motor 153 having a drive shaft 155, a motor clamp 157, screws 159, wires 161 and an electrical connector 163 corresponding to electric motor 103, drive shaft 109, motor clamp 105, screws 107, wires 113 and electrical connector 111, respectively.

Pivot assemblies 143 and 145 are positioned on base plate 13 such that mask bars 119 and 121 are parallel to and symmetrically disposed on either side of vertical cross hair 49.

Fourier mask 11 further includes a pair of standoffs 165 and 167 for mounting mask 11 on a support structure (not shown). Standoffs 165 and 167 are mounted on base plate 13 by screws 163.

As is evident, the spacing between mask bars 119 and 121 can be easily changed by rotating cross bar 117.

Thus, Fourier mask 11 includes three parallel equally spaced horizontal mask bars whose spacing from one another can be changed as desired and three parallel equally spaced vertical mask bars whose spacing to one another can also be changed as desired, in order to accommodate wafers having different repetitive pattern configurations.

Figure 6:
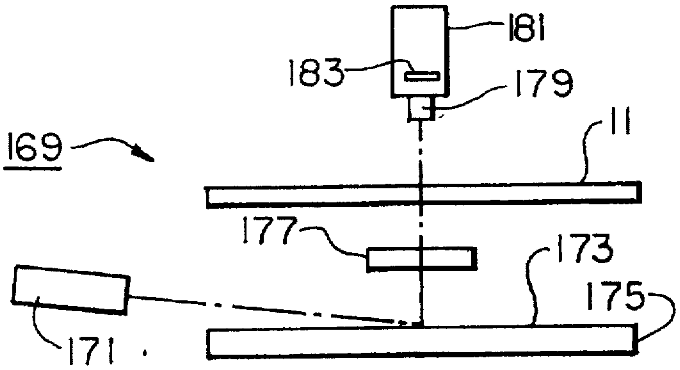
FIG. 6 is a simplified pictorial view of a system showing how the mask is used.
Figure 3:
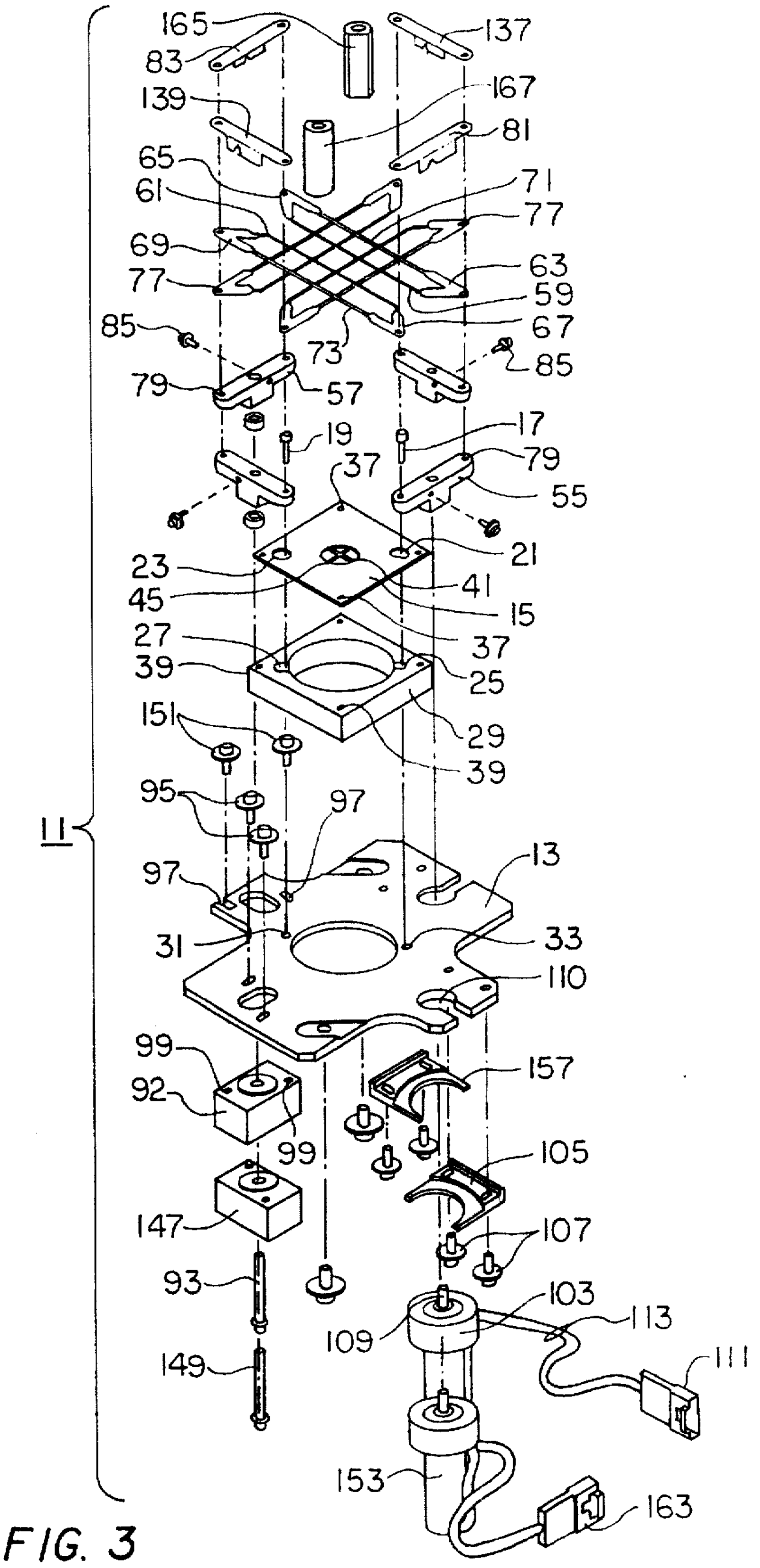
FIG. 3 is an exploded perspective view of the Fourier mask shown in FIG. 1.
Figure 5:
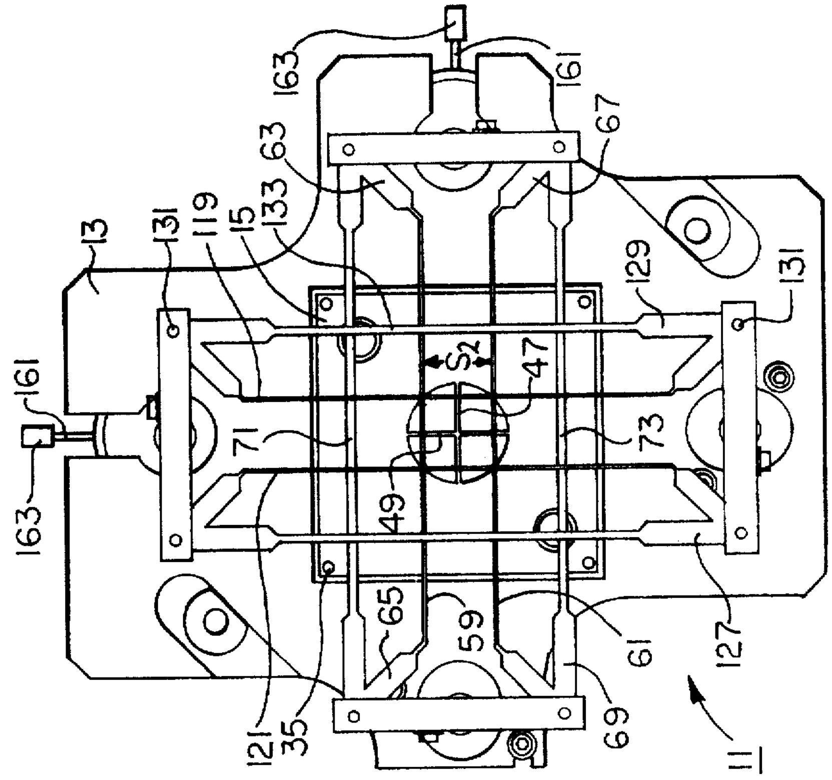
FIG. 5 is a plan view of the Fourier mask shown in FIG. 1, with the mask bars pairs spaced differently from that shown in FIG. 4.

Referring now to FIG. 6 there is shown a simplified pictorial view of an example an apparatus for detecting particles on the surface of a patterned semiconductor wafer using Fourier mask 11 of this invention, the apparatus being identified by reference numeral 169. Light from a laser 171 illuminates the front surface 173 of a patterned semiconductor wafer 175 at grazing angle of incidence. A lens 177 disposed above surface 169 forms a Fourier transform of light diffracted from surface 173 on mask 11 which is arranged to provide a pattern of mask bars corresponding to the Fourier transform of the patterned surface. Thus all of the light from surface 173 but not any light scattered from a particle on the surface will be masked off. A lens 179 of a camera 181 images surface 173 on the target 183 inside camera 181.

The embodiments of the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A Fourier mask comprising:

a. a base plate, b. an aperture plate mounted on said base plate, said aperture plate being provided with an aperture, a first four bar linkage, said first four bar linkage comprising a pair of parallel cross bars and a pair of parallel mask bars, said cross bars and said mask bars being pivotally interconnected end-to-end in a closed loop configuration, said mask bars being positioned over said aperture so as to function as a pair of parallel mask elements over said aperture, said mask bars having a combined width substantially less than the diameter of said aperture, d. a first pivot assembly for pivotally mounting one of said cross bars of said first four bar linkage on said base plate, and e. a second pivot assembly for pivotally mounting the other one of said cross bars in said first four bar linkage on said base plate, f. whereby, the spacing between said pair of parallel mask bars in said first four bar linkage can be changed by pivotally moving said cross bars in said first four bar linkage on said base plate.

2. A Fourier mask comprising:

a. a base plate, b. an aperture plate mounted on said base plate, said aperture plate being provided with an aperture, c. a first four bar linkage, said first four bar linkage comprising a pair of parallel cross bars and a pair of parallel mask bars, said cross bars and said mask bars being pivotally interconnected in a parallelogram shaped configuration, said mask bars of said first four bar linkage being positioned over said aperture so as to function as a first pair of parallel mask elements over said aperture, said mask bars of said first four bar linkage having a combined width substantially less than the diameter of said aperture, d. a first pivot assembly for pivotally mounting one of said cross bars in said first four bar linkage on said base plate, e. a second pivot assembly for pivotally mounting the other one of said cross bars in said first four bar linkage on said base plate, f. whereby, the spacing between said pair of parallel mask bars in said first four bar linkage can be changed by pivotally moving said cross bars in said first four bar linkage on said base plate, g. a second four bar linkage, said second four bar linkage comprising a pair of parallel cross bars and a pair of parallel mask bars, said cross bars and said mask bars being pivotally interconnected in a parallelogram shaped configuration, said mask bars of said second four bar linkage being positioned over said aperture so as to function as a second pair of parallel mask elements over said aperture, said mask bars of said second four bar linkage having a combined width substantially less than the diameter of said aperture, h. a third pivot assembly for pivotally mounting one of said cross bars in said second four bar linkage on said base plate, i. a fourth pivot assembly for pivotally mounting the other one of said cross bar in said second four bar linkage on said base plate, j. whereby, the spacing between said pair of parallel mask bars in said second four bar linkage can be changed by pivotally moving said cross bars in said second four bar linkage on said base plate, k. said mask bars in said first four bar linkage being disposed at right angles to said mask bars in said second four bar linkage.

3. A Fourier mask comprising:

a. a base plate, b. an aperture plate mounted on said base plate, said aperture plate being provided with an aperture, and c. a first four bar linkage, said first four bar linkage comprising a pair of parallel cross bars and a pair of parallel mask bars, said cross bars and said mask bars being pivotally interconnected in a closed loop configuration, said mask bars being positioned over said aperture so as to function as a pair of parallel mask elements over said aperture, said mask bars having a combined width substantially less than the diameter of said aperture, d. said first four bar linkage being mounted on said base plate whereby the spacing between said pair of parallel mask bars can be changed.

4. A Fourier mask comprising:

a. a base plate, b. an aperture plate mounted on said base plate, said aperture plate being provided with an aperture, c. a first four bar linkage comprising a pair of parallel cross bars and a pair of parallel mask bars pivotally interconnected in a parallelogram shaped configuration, said mask bars being positioned over said aperture so as to function as a first pair of parallel mask elements over said aperture, said mask bars of said first four bar linkage having a combined width substantially less than the diameter of said aperture, d. means for mounting said first four bar linkage on said base plate so that the spacing between the pair of parallel mask bars can be changed, e. whereby, the spacing between said pair of parallel mask bars in said first four bar linkage can be changed by pivotally moving said cross bars in said first four bar linkage on said base plate, f. a second four bar linkage, said second four bar linkage comprising a pair of parallel cross bars and a pair of parallel mask bars, said cross bars and said mask bars being pivotally interconnected in a parallelogram shaped configuration, said mask bars being positioned over said aperture so as to function as a second pair of parallel mask elements over said aperture, said mask bars of said second four bar linkage having a combined width substantially less than the diameter of said aperture, g. means for mounting said second four bar linkage on said base plate whereby the spacing between the pair of parallel mask bars can be changed, h. whereby, the spacing between said pair of parallel mask bars in said second four bar linkage can be changed by pivotally moving said cross bars in said second four bar linkage on said base plate, i. said mask bars in said first four bar linkage being disposed at right angles to said mask bars in said second four bar linkage.

5. A Fourier mask comprising:

a. a base plate, b. a first four bar linkage, said first four bar linkage comprising a pair of parallel cross bars and a pair of parallel mask bars, said cross bars and said mask bars being pivotally interconnected end-to-end in a closed loop configuration, c. a first pivot assembly for pivotally mounting one of said cross bars of said first four bar linkage on said base plate, d. a second pivot assembly for pivotally mounting the other one of said cross bars in said first four bar linkage on said base plate, whereby the spacing between said pair of parallel mask bars in said first four bar linkage can be changed by pivotally moving said cross bars in said first four bar linkage on said base plate, and e. an aperture plate fixedly mounted on said base plate, said aperture plate including a pair of fixed cross hairs.

6. The Fourier mask as claimed in claim 5 wherein said mask bars are parallel to and evenly spaced on either side of one of said fixed cross hairs.

7. A Fourier mask comprising:

a. an aperture plate, said aperture plate being provided with an aperture;

b. a first pair of parallel mask bars, said first pair of parallel mask bars having a combined width substantially less than the diameter of said aperture, and c. means for positioning said first pair of parallel mask bars over said aperture wherein the spacing between said first pair of parallel mask bars is adjustable.

8. The Fourier mask as claimed in claim 7 further comprising a fixed pair of cross hairs mounted in said aperture, said first pair of parallel mask bars being parallel to and evenly spaced on either side of one of said fixed cross hairs.

9. The Fourier mask as claimed in claim 8 further comprising a second pair of parallel mask bars, said second pair of parallel mask bars having a combined width substantially less than the diameter of said aperture, said second pair of parallel mask bars being disposed at right angles to said first pair of parallel mask bars and being parallel to and evenly spaced on either side of the other of said fixed cross hairs.

and means for positioning said second pair of parallel mask bars over said aperture wherein the spacing between said second pair of parallel mask bars is adjustable.

10. An apparatus for detecting particles on the surface of a patterned semiconductor wafer comprising:

a. means for illuminating a surface of the patterned semiconductor wafer;

b. a Fourier mask, said Fourier mask comprising i. an aperture plate, said aperture plate being provided with an aperture, ii. a first pair of parallel mask bars, said first pair of parallel mask bars having a combined width substantially less than the diameter of said aperture, and iii. means for positioning said first pair of parallel mask bars over said aperture wherein the spacing between said first pair of parallel mask bars is adjustable, c. means for forming a Fourier transform of light diffracted from the surface of the patterned semiconductor wafer on the Fourier mask; and d. means for detecting the light transmitted by the Fourier mask.

11. The apparatus as claimed in claim 10 wherein said Fourier mask further comprises a fixed pair of cross hairs mounted in said aperture, said first pair of parallel mask bars being parallel to and evenly spaced on either side of one of said fixed cross hairs.

12. The apparatus as claimed in claim 11 wherein said Fourier mask further comprises a second pair of parallel mask bars, said second pair of parallel mask bars having a combined width substantially less than the diameter of said aperture, said second pair of parallel mask bars being disposed at right angles to said first pair of parallel mask bars and being parallel to and evenly spaced on either side of the other of said fixed cross hairs, and means for positioning said second pair of parallel mask bars over said aperture wherein the spacing between said second pair of parallel mask bars is adjustable.

* * * * *